United States Patent [19]
Knoch et al.

[11] Patent Number: 4,923,465
[45] Date of Patent: May 8, 1990

[54] CARDIAC VALVE PROSTHESIS

[75] Inventors: Martin Knoch; Helmut Reul; Günter Rau, all of Aachen, Fed. Rep. of Germany

[73] Assignee: B. Braun Melsungen AG, Melsungen, Fed. Rep. of Germany

[21] Appl. No.: 387,694

[22] Filed: Jul. 31, 1989

[30] Foreign Application Priority Data

Aug. 25, 1988 [DE] Fed. Rep. of Germany ....... 3828781

[51] Int. Cl.$^5$ ............................................. A61F 2/24
[52] U.S. Cl. ........................................ 623/2; 137/527
[58] Field of Search ................... 623/2; 137/527, 527.8

[56] References Cited

U.S. PATENT DOCUMENTS

| | | | |
|---|---|---|---|
| 3,546,711 | 12/1970 | Bokros | 623/2 |
| 4,011,601 | 3/1977 | Clune | 623/2 |
| 4,123,805 | 11/1978 | Kramer | 623/2 |
| 4,159,543 | 7/1979 | Carpentier | 623/2 |
| 4,451,937 | 6/1984 | Klawitter | 623/2 |
| 4,488,318 | 12/1984 | Kaster | 623/2 |
| 4,775,378 | 10/1988 | Knoch et al. | 623/2 |
| 4,799,930 | 1/1989 | Knoch et al. | 623/2 |

FOREIGN PATENT DOCUMENTS 0113681  7/1984  European Pat. Off. ............... 623/2

*Primary Examiner*—Ronald L. Frinks
*Attorney, Agent, or Firm*—Spensley Horn Jubas & Lubitz

[57] ABSTRACT

In a cardiac valve prosthesis, the journal pins, by which the closing body is supported to be swiveled in the valve ring, are received in through holes of the valve ring and can be moved into different positions in these through holes. Thereby, the journal pins are subjected to a circumfluent blood streams, reducing the danger of thrombi being formed at the supporting areas.

17 Claims, 3 Drawing Sheets

CARDIAC VALVE PROSTHESIS

BACKGROUND OF THE INVENTION

1. Field of the Invention

The invention is directed to a cardiac valve prosthesis.

2. Description of Related Art

The natural cardiac valves are tricuspid or bicuspid valves which have two or three flaps, respectively, and, technically speaking, fulfill the function of nonreturn valves allowing the blood to pass in one direction but stopping it in reverse direction. If the natural cardiac valves are to be replaced by mechanical pendulum-disk type or tilting-disk type prostheses, there are inserted monocuspid or bicuspid valves wherein closing bodies, by the blood pressure or the blood flow, are movable within a valve ring which is sutured to the respective opening of the heart. Long-term use of such cardiac valve prostheses can result in massive problems, necessitating life-long administration of anticoagulants to the patient or replacement of the prosthesis. For example, there is the danger of thrombi occuring at the valve ring or at the fastening means for the closing body, which thrombi impair the easy action of the closing body and the fluid-tightness of the cardiac valve prosthesis. Further, body tissue can grow into the flow path of the blood. The danger of thrombi being formed is imminent particularly at the journal pins of the closing body which engage into the recesses of the valve ring. Therefore, particular precautions must be taken to safeguard the flowing movement of the blood around the journal pins and through the recesses receiving the journal pins.

U.S. Pat. No. 4,799,930 describes a cardiac valve prosthesis in which the journal pins of the valve ring are supported in articular sockets having at least one flushing channel leading therethrough. On the one hand, such an articular-socket structure is difficult to manufacture, and on the other hand, it does not provide the required mobility of the closing body.

In a cardiac valve prosthesis as known from European publication No. 0 113 681 A1, the wall of the valve ring is provided with recesses being larger in diameter than the journal pins of the closing body so that the journal pins, during the opening and closing movement of the closing body, perform a translatory movement. Said recesses are troughs or blind holes, with the front ends of the journal pins sweeping over the bottom of the recesses in the manner of a windshield-wiper when the valve ring is moved. Thereby, a wiping effect is obtained with each movement of the closing body. However, it is disadvantageous that not all of the surface portions are subjected to said wiping effect equally and that in the recesses, especially at their edges, there are generated areas of possible thrombi formation.

In known cardiac valve prostheses, recirculation flows and dead-water areas occur in the journaling areas of the closing bodies, resulting in insufficient wash-out of the contact areas between valve ring and closing body. Thrombi adhering to these areas provoke the danger of incomplete opening and closing movements.

It is an object of the invention to provide a cardiac valve prosthesis in which the generation of thrombi in the supporting areas, being especially susceptible to thrombi, is prevented.

SUMMARY OF THE INVENTION

In the cardiac valve prosthesis according to the invention, the recesses having the closing body supported therein are through holes. Since the diameter of these through holes is larger than the diameter of the journal pins, flow channels are generated so that a small part of the blood streaming into the valve ring laterally issues via said through holes and thus flows about the journal pins. This circumfluent blood movement, e.g. in case of an aortic valve prosthesis, occurs not only during the systole when the closing body is in its opening position but, to a slight extent, also during the diastole when the closing body is in its closing position. Therefore, the journal pins have blood flowing about them in both end positions, thus effecting continuous change of the respective supporting-pin areas being exposed to said circumfluent blood movement.

The invention is particularly suited for monocuspid cardiac valve prostheses but is also applicable for supporting the closing bodies of bicuspid cardiac valve prostheses. The transition surfaces from the closing body as well as from the valve ring to the respective supporting members have to be arranged in such a manner that, during the blood flow, the wall shearing-stresses at the valve surfaces are distributed as uniform as possible. At the same time, obstruction of the ring section in the opened state of the valve should be minimal. The supporting structures must not exert any considerable influence on the pressure distribution at the closing-body surface. This condition is normally fulfilled if no flow separations are caused.

According to a preferred embodiment, the passage of the closing body extends obliquely to the normal line of the inlet opening. Such an oblique arrangement of said passage enhances the flow deviation effected by the opened closing body. The longitudinal holes extend in parallel to the passage. Thereby, during opening, clamping of the edge of the closing body at the valve ring is prevented. The length of the valve ring can be reduced.

The journal pins need not necessarily be round or cylindrical. Particularly, this is not required because the swiveling angle of the closing body is limited. Only at least over this swiveling angle of ca. 70°, a cylindrical supporting surface is desirable. Therefore, also longitudinal journal-pin sections can be provided, being rounded at one end only. Also, it is not absolutely required that the through holes are longitudinal holes. Alternatively, the through holes can also be shaped as circular sectors. What is important is only that an allowance is left for the journal pins in the through holes, and that, during movement from the opened position to the closed position, there are exposed different circumferential areas, respectively, of the journal pins in the through holes.

BRIEF DESCRIPTION OF THE DRAWINGS

An embodiment of the invention will be explained in greater detail hereunder with reference to the drawings.

In the drawings

DESCRIPTION OF THE PREFERRED EMBODIMENTS

Figure 1:
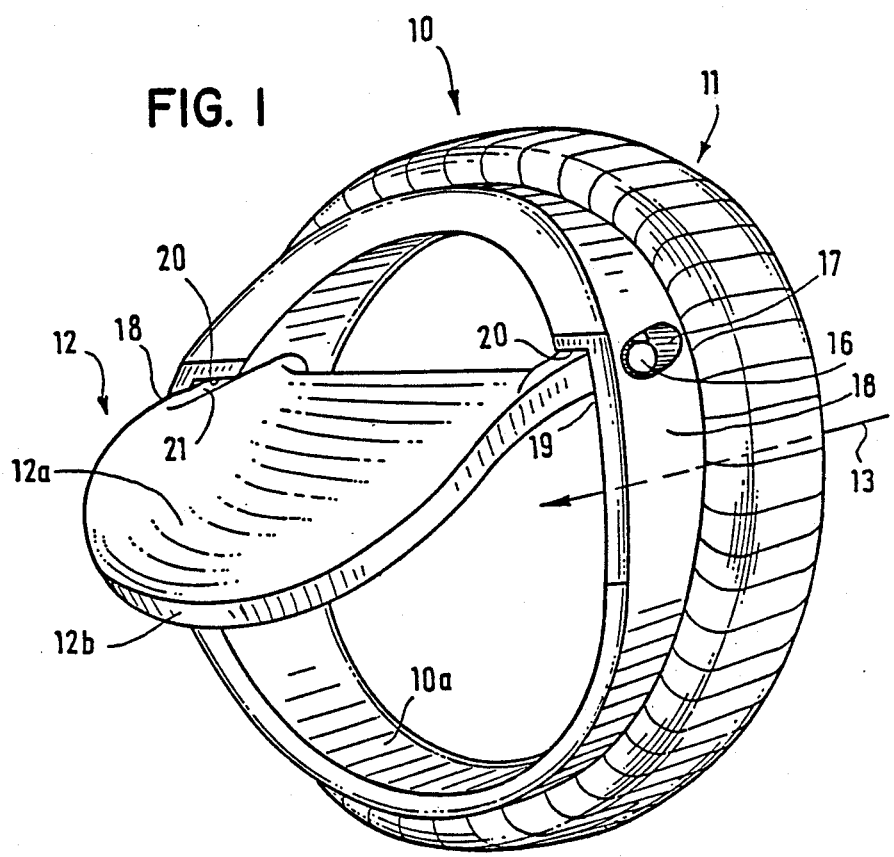
FIG. 1 is a perspective view of a preferred embodiment of the cardiac valve prosthesis of the present invention.

The monocuspid cardiac valve prosthesis, to be described by way of example, is provided with a substantially circular valve ring 10. To the circumference of valve ring 10, there is fastened a suture ring 11 for attaching the cardiac valve to the body tissue of the patient. At the valve ring 10, the valve-shaped closing body 12 is supported to be swiveled about an axis extending transversely to the ring axis. This swiveling axis is arranged at a distance from the ring axis so that the closing body 12 can be opened by the blood pressure acting in the direction of arrow 13, whereas it is brought into the closing position by blood pressure acting in the opposite direction.

The inner surface 10a of the valve ring 10 forms a substantially cylindrical passage the axis 14 of which extends under an angle (a) to the normal line of the inlet opening 15 of the valve ring. The axis 14 of said passage formed by inner surface 10a is substantially in parallel to the opened closing body 12.

Figure 2:
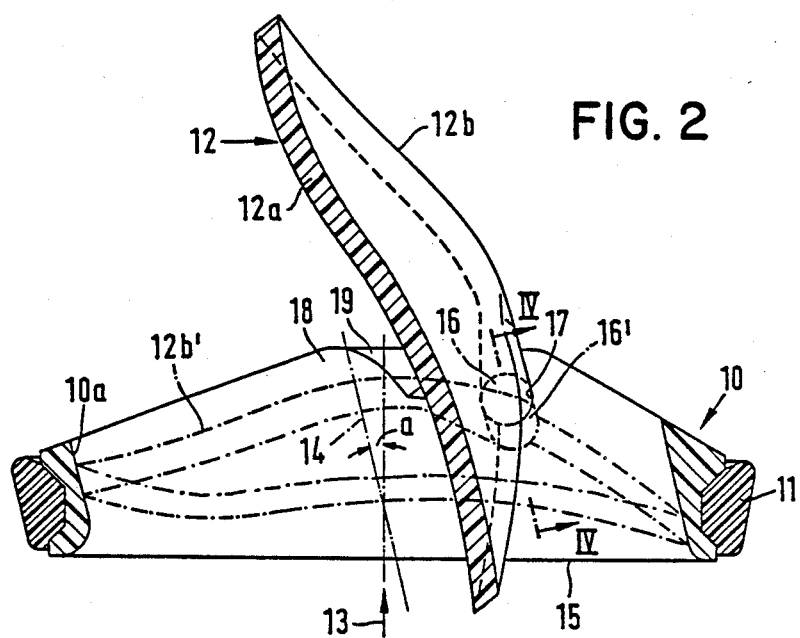
FIG. 2 is a longitudinal section of the cardiac valve prosthesis in the opened condition.

As FIG. 2 shows, the skeleton line of the section of the closing body—represented in hatched lines—is slightly curved in the manner of an S. The skeleton line is arranged in the central plane of the closing body, the central plane extending transversely to the support axis. Additionally, the closing body 12 is curved in lateral direction, i.e. its central portion 12a projects further against the flow direction according to arrow 13 than its edge portion 12b.

At the circumference of closing body 12, two journal pins 16 are arranged, projecting in opposite directions. The common axis of said journal pins 16 forms the swiveling axis of the closing body. Each of the journal pins 16 is seated in a through hole 17 passing through the wall of valve ring 10. In the described embodiment, the journal pins 16 are of cylindrical shape. The width of the through holes is only slightly larger than the diameter of the journal pins 16 so that the journal pins 16 can turn in the through holes 17 unhindered by clamping. The through holes 17 are formed as longitudinal holes, their length being substantially twice as large as the diameter of the journal pins 16. Since the suture ring 11 surrounds the valve ring 10 on the entire circumference thereof and since the through holes 17 must not be covered by suture ring 11, the valve ring has its downstream end provided with two opposing flaps 18 in which the through holes 17 are arranged such as not to be covered by the suture ring 11.

The through holes 17, provided as longitudinal holes, run parallel to the axis 14 of the ring passage. In the opening position of closing body 12, the journal pins 16 are pressed against the downstream end 17a of through hole 17, whereas, when the closing body is in its closed position, they are pressed against the upstream end 17b. Thus, the closing body, in addition to its rotatory movement about the axis of the journal pins 16, also performs a translatory movement in the direction of the longitudinal holes. The ends 17a and 17b of the through holes are rounded in such a manner that they support the abutting area of the circumference of journal pin 16 by their full surfaces. In this manner, surface pressures are kept low.

Figure 4:
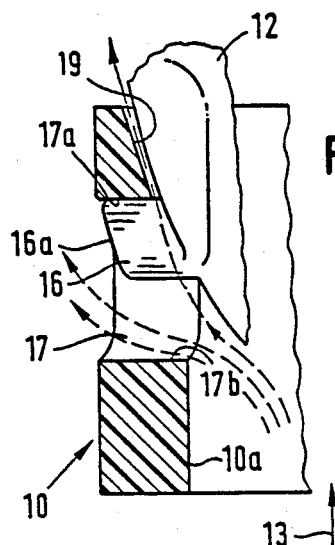
FIG. 4 is a sectional view of a supporting area along the line IV—IV of FIG. 2.

As FIG. 4 shows, all of the journal pins 16 have oblique end faces 16a; at the same time, however, the journal pins are entirely received in the through holes 17. This means that the journal pins 16 do not project beyond the outer contour of valve ring 10.

Figure 5:
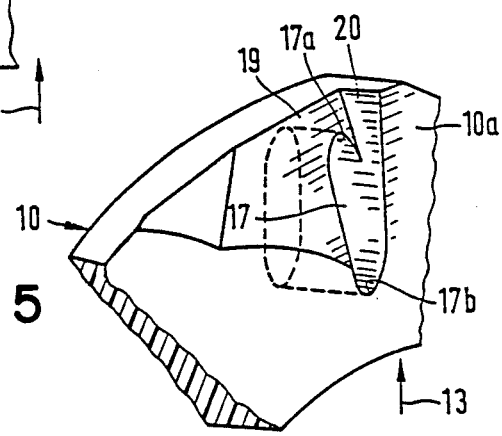
FIG. 5 is a perspective view of the supporting area without the closing body mounted, and FIG. 6 schematically shows the manner in which the closing body is being mounted into the valve ring.
Figure 6:
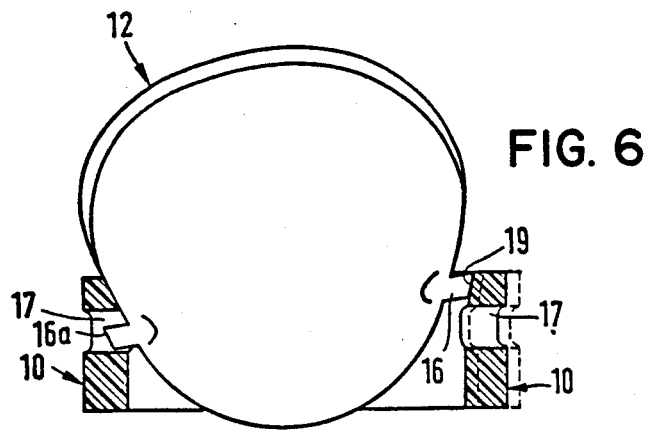

According to FIG. 5, the valve ring 10 has each of its supporting areas provided with a recess 19 arranged at the inner circumference of the valve ring and being limited by an abutting surface 20 extending tangentially to the longitudinal hole 17. This orientation of the abutting surface 20 safeguards that the closing body 12, independently of the position of the journal pins 16 in the through holes 17, always maintains the same opening angle. The depth of the recess 19 is largest at the downstream edge of the valve ring 10, and the depth decreases in upstream direction. When the closing body 12 is being mounted into valve ring 10 from the downstream side, one of the journal pins 16 is first inserted into the corresponding through hole 17. Then, the oblique surface 16a of the other journal pin 16 is set against the recess 19 according to FIG. 6. When advancing the closing body 12, a slight radial deformation of valve ring 10 is effected, indicated by broken lines in FIG. 6. The oblique surface 16a of journal pin 16 slides over the oblique surface of recess 19 in full face-to-face contact until the journal pin 16 is locked into the through hole 17. By the oblique surfaces of journal pin 16 and recess 19 sliding on each other, damages to the closing body and the valve ring are prevented while the closing body is being mounted.

Figure 3:
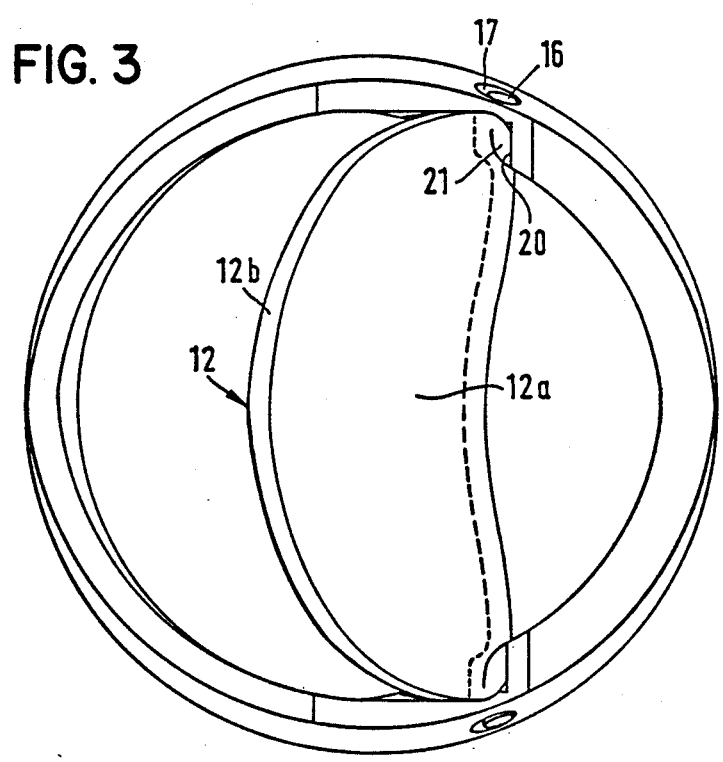
FIG. 3 is a plan view on the cardiac valve prosthesis as shown in FIG. 2.

At the downstream rear face of closing body 12 and adjacent to the journal pins 16, flattend abutting faces 21 (FIG. 3) are provided which, in the opening position of the closing body, come into plane abutment with the abutting faces 20 and thus limit the opening position. The closing position of the closing body is limited in that the edge 12b abuts against the inner surface 10a of valve ring 10.

In FIG. 2, the solid lines represent the closing body in its opened position. The broken lines represent the course of the edge 12b of closing body 12 in the closed position, designated by 12'. In the closed condition, the journal pins 16 in the through holes 17 maintain the position designated by 16', i.e. they are supported at the upstream ends 17b of the longitudinal holes.

FIG. 4 shows the path of the blood flow in the opening condition of the closing body 12 at the journaling area. As can be seen from the Figure, a large portion of the blood stream issues to the outside via through hole 17 and simultaneously flows around pin 16, and part of the blood stream washes through the gap between the edge of closing body 12 and recess 19.

We claim:

1. A cardiac valve prosthesis having a valve ring in which at least one closing body is supported to be swiveled, and journal pins projecting from the closing body and engaging into recesses at the inner surface of the valve ring, said recesses being larger in diameter than the journal pins in such a manner that the journal pins, when the closing body is swiveled, fill different areas of the recesses, characterized in that the recesses are through holes being open towards the exterior of the valve ring.

2. A cardiac valve prosthesis according to claim 1, characterized in that the through holes are longitudinal holes having such a length that the journal pins can be shifted within the through holes.

3. A cardiac valve prosthesis according to claim 1, characterized in that the inner surface of the valve ring forms a passage having its axis extending under an angle obliquely to the normal line of the inlet opening of the valve ring, the angle of said oblique position being arranged in a plane extending at a right angle to the axis of the journal pin such that the axis of the passage extends substantially in parallel to the opened closing body.

4. A cardiac valve prosthesis according to claim 2, characterized in that the longitudinal holes extend parallel to the axis of the passage.

5. A cardiac valve prosthesis according to claim 1, characterized in that the closing body, at its downstream end and adjacent to the journal pins, is provided with abutting faces (21) which cooperate with abutting faces (20) of the valve ring (10) and limit the opening movement of the closing body (12) to an angle smaller than 80°.

6. A cardiac valve prosthesis according to claim 1, characterized in that the journal pins do not project beyond the outer contour of the valve ring and have oblique end faces which, in the opening position of the closing body, recede in upstream direction.

7. A cardiac valve prosthesis according to claim 5, characterized in that oblique surfaces are provided at the inner surface of the valve ring and adjacent to the through holes, which oblique surfaces recede in flow direction towards the exterior and adjoin abutting surfaces for the closing body.

8. A cardiac valve prosthesis according to claim 1, characterized in that the closing body has its skeleton line curved in the manner of an S and is also curved in transverse direction.

9. A cardiac valve prosthesis comprising:
a valve ring having an interior surface, an exterior surface and a through hole opened to the exterior surface,
a closing body having a journal pin positioned to engage the through hole, the closing body being moveable relative to the valve ring between an open position and a closed position,
the through hole and the journal pin being configured such that the journal pin occupies different regions of the through hole when the closing body is moved between the open position and the closed position,
whereby different regions of the through hole and journal pin are exposed and subjected to circumfluent blood flow when the closing body is moved between the open position and the closed position, thereby reducing the risk of thrombi formation.

10. A cardiac valve prosthesis according to claim 9, wherein the through hole defines a substantially longitudinal axis and has a length which is sufficient to enable the journal pin to shift position within the through hole when the closing body is moved between the open position and the closed position.

11. A cardiac valve prosthesis according to claim 9, wherein
the journal pin defines a journal pin axis,
the valve ring defines an inlet opening having a line normal thereto,
the interior surface of the valve ring defines a passage having an passage axis,
the passage axis and the line normal to the inlet opening define an angle,
the angle being arranged in a plane which extends at a right angle to the journal pin axis,
whereby the passage axis and the closing body are substantially parallel when the closing body is in the open position.

12. A cardiac valve prosthesis according to claim 11, wherein the through hole defines a substantially longitudinal axis substantially parallel to the passage axis.

13. A cardiac valve prosthesis according to claim 9, wherein the valve ring and the closing body define a relative angle, and further comprising limitation means for limiting the relative angle between the valve ring and the closing body in the open position to an angle smaller than 80°.

14. A cardiac valve prosthesis according to claim 9, wherein the journal pin is configured to not project beyond the exterior surface of the valve ring and wherein the journal pin defines an oblique end face, the oblique end face being configured to recede toward the direction of blood flow when the closing body is in the open position.

15. A cardiac valve prosthesis according to claim 14, wherein the closing body defines an abutting surface, the interior surface of the valve ring defines an oblique surface adjacent to the through hole, the oblique surface being configured to recede in the blood flow direction towards the exterior surface of the valve ring, the oblique surface adjoining the abutting surface of the closing body.

16. A cardiac valve prosthesis according to claim 9, wherein the closing body defines an S-shaped skeleton line curved in a transverse direction.

17. A cardiac valve prosthesis according to claim 13, wherein the limitation means comprises an abutting face provided on the closing body adjacent the journal pin and a cooperating abutting face provided on the valve ring.

* * * * *